(12) United States Patent
Favie et al.

(10) Patent No.: US 10,285,722 B2
(45) Date of Patent: May 14, 2019

(54) MICRODERMABRASION DEVICE AND MICRODERMABRASION METHOD

(71) Applicants: Alain Favie, Brest (FR); Armand Boloorchi, Brest (FR)

(72) Inventors: Alain Favie, Brest (FR); Armand Boloorchi, Brest (FR)

( * ) Notice: Subject to any disclaimer, the term of this patent is extended or adjusted under 35 U.S.C. 154(b) by 297 days.

(21) Appl. No.: 15/125,900

(22) PCT Filed: Mar. 16, 2015

(86) PCT No.: PCT/EP2015/055383
§ 371 (c)(1),
(2) Date: Sep. 13, 2016

(87) PCT Pub. No.: WO2015/136116
PCT Pub. Date: Sep. 17, 2015

(65) Prior Publication Data
US 2017/0014145 A1    Jan. 19, 2017

(30) Foreign Application Priority Data

Mar. 14, 2014 (FR) ...................... 14 52114

(51) Int. Cl.
*A61B 17/32* (2006.01)
*A61B 17/54* (2006.01)
*A61M 35/00* (2006.01)
*A61N 5/06* (2006.01)
*A61B 17/00* (2006.01)

(52) U.S. Cl.
CPC .............. *A61B 17/32* (2013.01); *A61B 17/54* (2013.01); *A61M 35/00* (2013.01); *A61N 5/0616* (2013.01); *A61B 2017/00734* (2013.01); *A61B 2017/00747* (2013.01); *A61B 2017/320004* (2013.01); *A61B 2017/320008* (2013.01); *A61B 2017/320028* (2013.01); *A61N 2005/0652* (2013.01)

(58) Field of Classification Search
CPC ...... A61B 17/32; A61B 17/54; A61N 5/0616; A61M 35/00
See application file for complete search history.

(56) References Cited

U.S. PATENT DOCUMENTS

2008/0103563 A1   5/2008   Powell et al.
2010/0326456 A1   12/2010  Song

FOREIGN PATENT DOCUMENTS

| AU | 2011265418 A1 | 1/2012 |
| EP | 0 381 962 A1 | 8/1990 |
| WO | 2006/045149 A1 | 5/2006 |
| WO | 2014/169237 A1 | 10/2014 |

OTHER PUBLICATIONS

International Search Report, dated Apr. 17, 2015, from corresponding PCT Application.

*Primary Examiner* — Richard G Louis
(74) *Attorney, Agent, or Firm* — Young & Thompson (57) ABSTRACT

A microdermabrasion device (1) includes: a detachable tip (11) including at least one abrasive element (112), the abrasive element (112) being provided such as to be applied onto the surface of the skin; a body having a vibrating element, the vibrating element being capable of making the detachable tip (11) vibrate; and a tip holder (12) that is securely attached to the body. The device is characterized in that the detachable tip (11) includes a deformable element (113) that is positioned between the abrasive element (112) and the tip holder (12).

17 Claims, 9 Drawing Sheets

MICRODERMABRASION DEVICE AND MICRODERMABRASION METHOD

TECHNICAL FIELD AND STATE OF THE ART

The present invention relates to a device for microdermabrasion of the skin in the field of cosmetic care, notably intended for non-physician cosmetic care professionals.

Microdermabrasion is a method consisting of removing a very superficial layer of skin, consisting of dead cells. Microdermabrasion also helps smooth the skin. Microdermabrasion unifies skin tone and makes the skin more radiant through the removal of dead cells and by promoting the natural process of tissue repair. Microdermabrasion is primarily used on the face, back of the hands, neck, cleavage, breast stretch marks, belly stretch marks, stretch marks on the hips and buttocks, and in areas such as the arms or thighs, primarily to improve skin texture, reduce imperfections or densify and tighten the skin.

Besides the stratum corneum of the skin and dead skin cells, microdermabrasion removes the upper layer of the epithelium, while remaining a distance from epithelial basal membrane.

Document WO 2006/045149 discloses a dermabrasion device comprising a vibrating body and an interchangeable tip having an abrasive surface. It allows the epidermal layer to be reduced in order to create new skin. However, this device is:
- difficult to handle,
- does not ensure good operational hygiene, and
- does not ensure good contact between the abrasive surface and the skin.

DESCRIPTION OF THE INVENTION

The invention seeks to overcome the drawbacks of the prior art and for this purpose relates to a microdermabrasion device comprising:
- a detachable tip (11) including at least one abrasive element (112), said abrasive element (112) being provided so as to be applied onto the surface of the skin,
- a body comprising a vibrating means, said vibrating means being capable of making the detachable tip (11) vibrate,
- a tip holder (12) that is securely attached to the body, noteworthy in that the detachable tip (11) comprises a deformable element (113) positioned between the abrasive element (112) and the tip holder (12), said detachable tip (11) comprises a protective element (111) positioned at the end of the detachable tip and said protective element (111) is in the shape of a half-sphere or of a flattened half-sphere.

The device improves the ease of use on the skin and is suitable for use in all areas of the body. The deformable element sweeps over the skin when using the device of the invention. In addition, the deformable element allows the abrasive element to be adapted in the shape of the skin owing to its deformation under pressure.

The protective element protects the surface of the skin from the edge of the abrasive element.

The term "deformable element" designates an element made of a deformable material that regains its original shape when the stress applied to it disappears.

The invention is advantageously implemented according to the embodiments described below, which are to be considered individually or in all technically operative combinations.

According to one aspect of the invention, the deformable element is made of elastomer with a Shore hardness of between 10 and 30. Shore hardness is defined by standards ISO 868 and 7619 on a scale of 0 to 100, from soft to hard. The hardness is a function of the elasticity of the material.

For safety purposes, the hardness is chosen so that excessive pressure stops the vibration and has no effect on the skin.

According to another aspect of the invention, in a sectional plane of the device containing the longitudinal axis of the body and the longitudinal axis of the tip holder, the longitudinal axis of the tip holder and the longitudinal axis of the body form an angle between 90° and 270°, preferably 135°. This angle between the detachable tip and the body increases the maneuverability of the object of the invention and the comfort of the user.

According to another embodiment, the device comprises a pivot connection between the tip holder and the body of the device, the axis of said pivot connection being contained in a plane orthogonal to the longitudinal axis of the body and passing through a point of intersection of the longitudinal axis of the tip holder with the longitudinal axis of the body.

The pivot connection orients the detachable tip relative to the body and adapts the device to the various positions and skin surfaces.

Advantageously, the body of the deformable element is oval, triangular, polygonal with at least five sides, or a circle, having a hole in the center into which the tip holder can be adapted.

According to a variant of the device according to the invention, the vibrating means comprises a motor driving in rotation an element equipped with an unbalancing mass.

In this latter variant, the device according to the invention comprises means for varying the rotation speed of the motor between 0 rpm and 12,000 rpm.

According to another variant, the device comprises at least lighting means, particularly a light emitting diode whose wavelength is between 400 and 900 nm and whose fluence is between 3 and 4 J/cm$^2$.

According to this variant, the wavelength is between 570 and 630 nm.

A Light-Emitting Diode, or LED, is an opto-electronic component capable of emitting light when an electric current passes through it.

The fluence (e.g., 3.4 J/cm$^2$) ensures good application efficiency of the light-emitting diode.

According to another variant, the deformable element comprises a cavity arranged therein to receive a volume of a creamy material, such as a soothing cream.

The cavity is thus compressed when in use, which pushes the cream out.

According to another variant of the present invention, the device comprises sealing means. In this manner, the device can be cleaned by running it under water.

According to another variant of the present invention, the abrasive element includes a fastening means such as glue or Velcro, arranged to maintain the abrasive element in position on the deformable element.

Also according to a variant, the abrasive element is a single-use tape, arranged to be positioned around the deformable element and a part of said tape can be detached to allow the abrasive element to be removed.

According to embodiments, the detachable tip is rotatably mobile about the longitudinal axis of the tip holder.

According to embodiments, the detachable tip is driven in rotation by a rotating means. The rotating means is a motor whose axis of rotation is connected directly or indirectly (e.g. the shaft of the motor is connected to a bevel gear with detachable tip).

The invention also relates to a microdermabrasion method for non-therapeutic cosmetic treatments comprising the following steps:
  a) placement of a detachable tip on the device according to the invention,
  b) vibration of the abrasive element on the surface of the skin, for a duration of 1 to 30 minutes over a surface area in the order of 50 to 300 cm$^2$.

According to a variant, the method comprises a step c), after step b), involving the removal of the abrasive element and the application of a soothing cream on the surface of the skin for a period of 2 to 20 minutes.

Owing to this device, an improvement in skin texture and enhanced facial radiance is observed following the first session. The skin texture is immediately refined and the boost in radiance is instantaneous. With a sufficient number of sessions (between 5 and 10 sessions during the initial phase and regular follow-up sessions) the results are comparable to and even better than existing chemical (peeling) or physical (laser) means.

Throughout the microdermabrasion sessions, combined with massages and a light wave, for the face, fine lines are flattened and skin surface defects are reduced. The skin appears younger, smoother and more uniform, as well as on the body where the skin appears younger, denser and more toned.

If used regularly, the long-term effects are:
improved skin texture,
an increase in the level of collagen and epithelial cells, and therefore enhanced skin flexibility, thickness and quality.

Generally speaking, the invention can slow the effects of aging of the skin at depth and always maintain surface skin "new". It slows down and attenuates the appearance of age-related imperfections on the skin, thanks to the resultant smoothing of the skin.

According to another variant, the method includes a step d) prior to step a), of removing the abrasive element from a sealed bag and placing said abrasive element on the detachable tip. In this manner, the abrasive element is single-use which guarantees operational hygiene each time.

BRIEF DESCRIPTION OF FIGURES

Other features and advantages of the invention will emerge more clearly on reading the description given hereafter with reference to the appended drawings. These examples are given for the purpose of illustration and are not limiting. The description is to be read in reference to the accompanying drawings in which.

DESCRIPTION OF EMBODIMENTS OF THE INVENTION

The microdermabrasion device is dual-use: microdermabrasion and massage.

Figure 1:
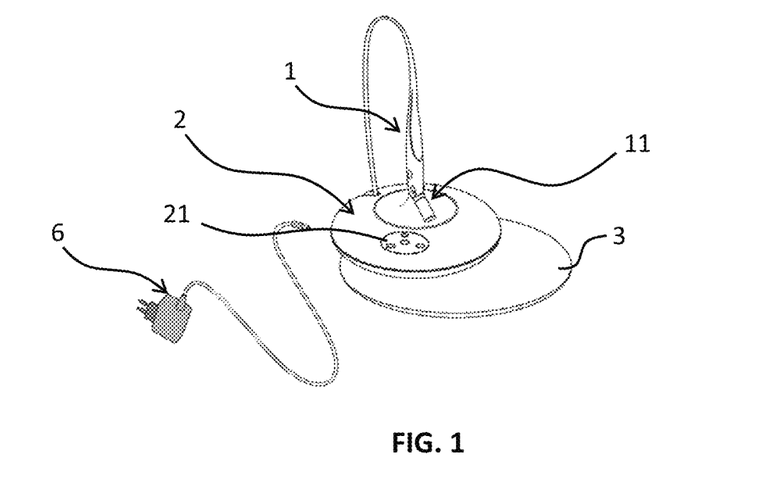
FIG. 1 shows an exemplary embodiment of the invention in a perspective view.

FIG. 1 shows the microdermabrasion device 1 mounted on the base 2. The device 1 comprises a detachable tip 11. This figure shows the power supply (transformer 6) external to the device 1 which powers the device or a support to the device. This figure also shows an interface 21 that allows the device 1 to be controlled and notably to vary the vibration.

In an exemplary embodiment, the detachable tip 11 is elongated in shape.

The transformer 6 (external power supply) can be connected to the base, to the support or to the device 1 (this variant will be described below).

According to another example of an embodiment, the device comprises:
  either an internal power supply, such as a battery, and a control selected among the motor on/off switch, a motor speed control or a control with a preset speed,
  or a base arranged to receive the device, said base comprising an interface selected among the motor on/off switch, a motor speed control or a control with a preset speed.

According to another example, said device comprises an external power supply connected either to the device or to the base.

Also, according to another example, the base is arranged to be attached to a support by connecting means. The connecting means conveys electricity to the base so as to electrically power the device, the support comprising a power supply. The connecting means also helps to attach the base to the support.

Figure 2:
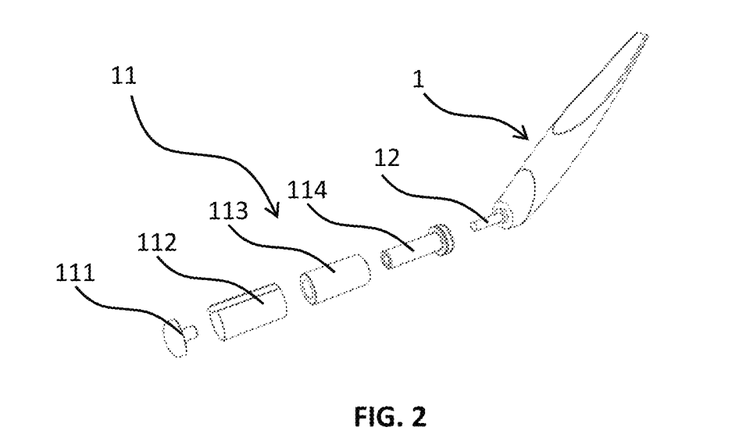
FIG. 2 shows an exploded view of an exemplary embodiment of the device according to the invention.

FIG. 2 shows a detachable tip 11 comprising several elements. A protective tip 111 is placed at the end of the detachable tip 11. An abrasive element 112 allows the device to be used for microdermabrasion. The abrasive element 112 is adapted to be applied to the surface of the skin.

The abrasive element 112 is sandpaper whose grain is between 100 and 600 grains per square meter. The abrasive element 112 is positioned around a deformable element 113.

In another embodiment, the abrasive element 112 comprises a fastening means, such as glue or Velcro. This fastening means is adapted to hold the abrasive element 112 in position on the deformable element 113.

The deformable element 113 is an elastomer, for example. This deformable element 113 is optimized with a measured density to render the microdermabrasion phase optimum and comfortable. According to the Shore hardness scale, the measurement of the elastomer is between 10 and 30, preferably 18.

In another example of the invention, the deformable element 113 has a cream contained in cavities. These cavities are able to receive a certain amount of a cream, such as a regenerative, soothing, or astringent cream, etc.

FIG. 2 also shows the rigid center 114 which is adapted to be positioned on the tip holder 12. The detachable tip 11 is positioned on a tip holder 12 of the device 1. The rigid center 114 is hollowed out in the center in the shape of the tip support 12. As shown in FIG. 2, the tip holder 12 is cylindrical in shape, thus the rigid center has a cylindrical bore. According to a variant, the tip holder 12 may be square shaped or have a flat surface for better transmitting the vibration. The rigid center 114 has a reversed shape of the tip holder 12.

It is also possible that the rigid center 114 and the deformable element 113 is bi-injected so as not to dissociate the rigid center 114 from the deformable element 113.

In another embodiment, the protective element 111 and the deformable element 113 are integral with one another.

The protective element 111 protects the patient from application of the tip on the skin. It also prevents the edge of the abrasive element 112 from injuring the patient. For example, the protective element 111 has a half-sphere or a flattened half-sphere shape as shown in FIG. 2.

In an exemplary embodiment, the protective element is in a central position on the tip. The protective element has a relatively smooth surface to avoid injuring the patient.

Figure 3:
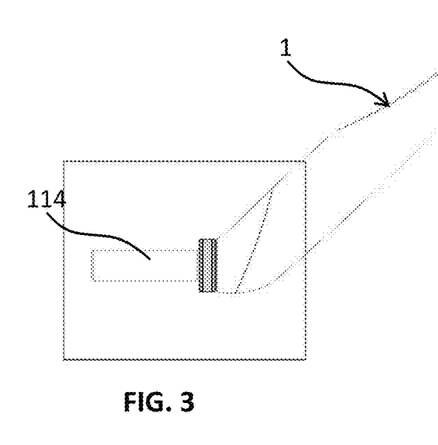
FIGS. 3 and 4 show a detailed view of the detachable tip of the device according to an exemplary embodiment of the invention.
Figure 4:
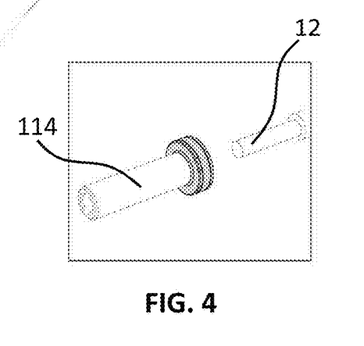

FIGS. 3 and 4 show the step where the detachable tip is fitted onto the tip holder 12. The rigid center 114 is shown. The rigid center 114 allows the detachable tip 11 to be fitted onto the tip holder 12. During the fitting step (not shown), a ring or a pin is broken off to prevent reuse. This fitting allows the detachable tip 11 to be securely attached to the device 1 in order to properly transmit the vibrations of the device 1 while operating. For example, the detachable tip 11 is inserted and rotated to connect with a position blocker. Performing such a movement will create a noise to inform the user that the detachable tip 11 is in position and secured to the device 1. In this manner, single-use is guaranteed to ensure the quality of the tip with respect to hygiene and safety.

Prior to installing the detachable tip 11 on the tip holder 12. The detachable tip 11 is contained in a sealed bag. In this way, hygiene is guaranteed until the bag is opened.

Figure 5:
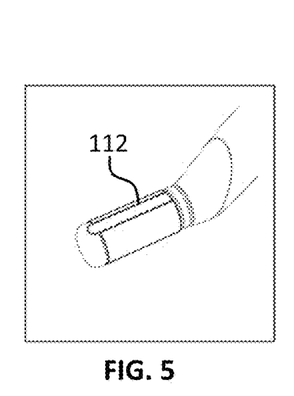
FIGS. 5 to 7 show how to remove the abrasive part of the detachable tip.
Figure 6:
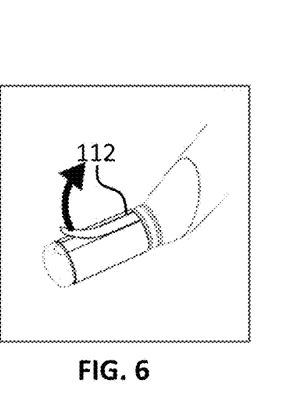
Figure 7:
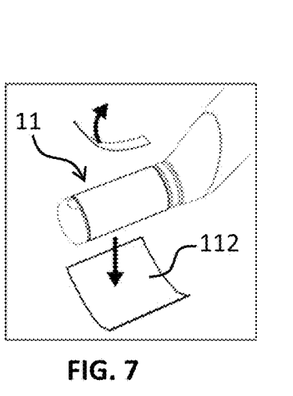
Figure 8:
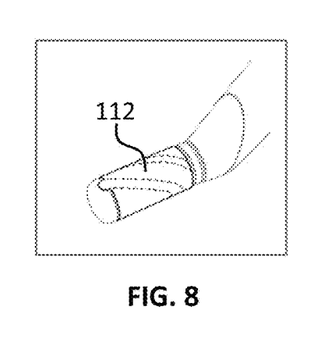
FIG. 8 shows another exemplary embodiment of the invention according to FIG. 5,
FIGS. 9 and 10 show different shapes of the detachable tip.

FIGS. 5 to 7 show a step of removing the abrasive element 112. For example, the abrasive element is an interchangeable tape arranged to be positioned around the deformable element 113. The tape is detachable to allow the abrasive element to be removed. For example, the tape comprises a tab. The tab may be over its entire length or twisted around the abrasive element 113, as shown in FIG. 8. In a variant, only the abrasive element is replaced; the deformable element 113 and the rigid center 114 remain in position on the tip holder 12.

Firstly, the tab must be identified. Secondly, the tab is removed in order to remove the abrasive element 112 from the detachable tip 11. The purpose of this step is to pass from the microdermabrasion step to the massage step. The microdermabrasion step is performed by the abrasive element 112 and the massage step is performed by the deformable element 113. The deformable element 113 is used for the massage phase.

According to a variant, the various elements of the device 1, such as the detachable tip 11, are injection molded with bioplastics (bio-sourced, biodegradable, compostable plastic). In this manner, using a detachable (single-use) tip 11 allows them to be recycled.

Figure 9:
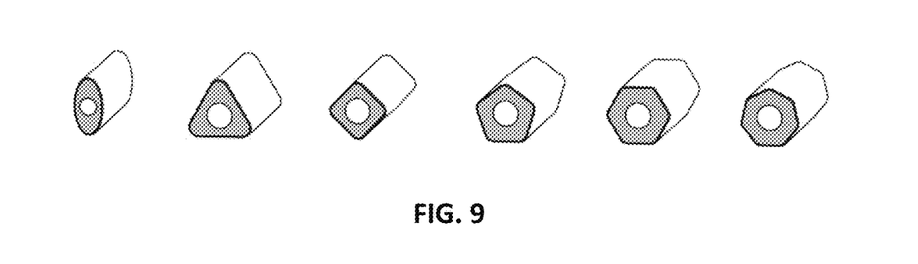
Figure 10:
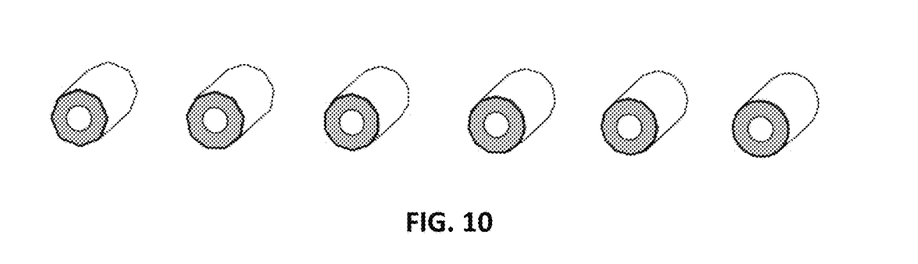

FIGS. 9 and 10 offer a perspective view of the various shapes of the detachable tip 11. The deformable element 113, securely attached to the rigid center 114, is an oval, a triangle, a square, a polygon with at least five sides, or a circle. These figures show that the deformable element is integral with the rigid center 114. In this manner, the transmission of vibrations is ensured.

Figure 11:
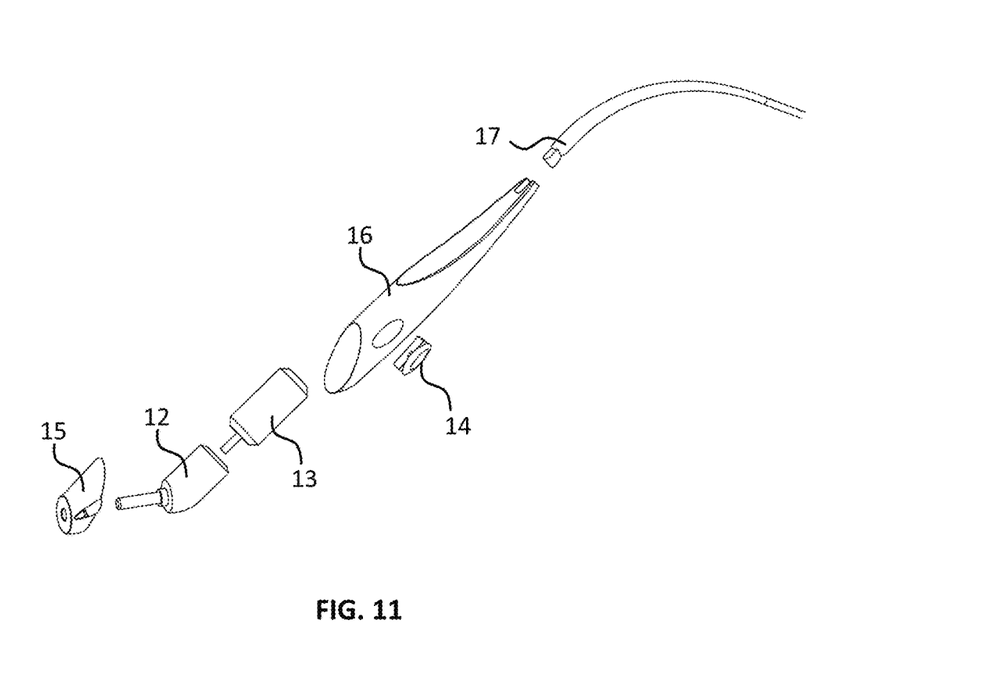
FIG. 11 shows an example of the body of the device according to the invention.

FIG. 11 shows the various elements of the device 1. The tip holder 12 is shown which cooperates with a motor 13.

The motor 13 drives a vibrating means in rotation, such as a mass arranged eccentrically in relation to the axis of rotation of the motor, to create the vibration.

In an exemplary embodiment, a switch 14 is used to vary the control of the motor 13. In another example, the interface 21 on the base 2 can vary the rotation speed of the motor. In an exemplary embodiment, a switch 14 is used to start and stop the motor. A cap 14 covers the tip holder 12. The cap 15 does not cover the tip holder so that it can receive the detachable tip.

In a variant, the cover is equipped with a light, such as an LED, which can produce a light in the order of 400 to 900 nm, preferably in the order of 570 to 630 nm. In a variant, an LED is positioned on each side of the cap 15. In another variant, the cover has an LED on the underside only. In another exemplary embodiment, an LED is positioned on top of the cap 15.

Clinical trials use sufficiently penetrating wavelengths around 600 nm or in the infrared spectrum, with fluence (delivered dose) from 1 to 20 $J/cm^2$ and irradiance (power density or intensity) varying according to the distance from the light source and the size of the spot from 5 to 50 $mW/cm^2$.

The photo-biological effects depend on the choice of the irradiation parameters: the wavelength, delivered dose (fluence), irradiance (power density or intensity), irradiation time (exposure time), continuous or pulsed delivery mode with possible combinations (pulse time-pause time) to infinity for the latter mode.

In another exemplary embodiment, the LEDs illuminate the bottom and sides of the detachable tip. In this example, there is no LED on top as the detachable tip would hide the light beam.

The device uses multiple wavelengths of light.

In an exemplary embodiment, the interface 21 or the device 1 has three buttons to select three colors, such as yellow at 588 nm, orange at 601 nm and red at 628 nm.

FIG. 11 also shows overmolding of the cable 17 that facilitates the handling of the device 1 by preventing the cable 17 from falling onto the device 1. The overmolding affords the cable 17 a rounded shape.

Figure 12:
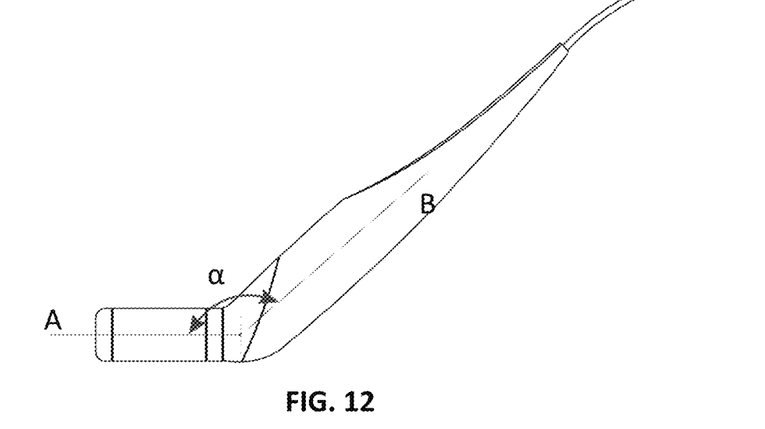
FIG. 12 shows a side view to show the angle between the detachable tip and the body of the device.

FIG. 12 shows an angle α between the longitudinal axis A of the detachable tip 11 and the longitudinal axis B of the device 1.

The longitudinal axis A of the detachable tip 11 (as shown in the figure) is defined at the intersection of "horizontal plane" of the detachable tip 11 defined in the conventional sense in the terrestrial reference and the "transversal plane" defined along the axis perpendicular to the horizontal plane.

The longitudinal axis B of the device 1 (as shown in the figure) is defined at the intersection of "horizontal plane" of the device 1 defined in the conventional sense in the terrestrial reference and the "transversal plane" defined along the axis perpendicular to the horizontal plane.

As shown in FIG. 12, the angle α is 135°.

Figure 13:
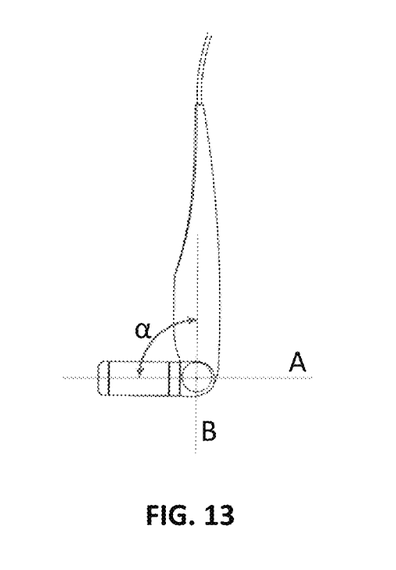
FIGS. 13 and 14 show a view of another example of the invention.

In a variant of the invention, FIG. 13 represents the angle α at 90°. In the same variant, it is possible to have an angle α at 270°. In this variant, the angle α can vary from 90° to 270°. The device 1 is connected to the detachable tip 11 by a pivoting element. A pivot connection is arranged between the tip holder 12 and the device 1 (or the body of the device, as shown in this figure). The pivot connection passes through an axis of rotation contained in a plane orthogonal to the longitudinal axis of the body of the device 1 and passing through a point of intersection of the longitudinal axis of the tip holder and the longitudinal axis of the body.

In a variant, the pivot connection is blocked to maintain the position according to preferred angle α. In this manner, the device can adapt to the treatment area where the skin is difficult to access.

Figure 14:
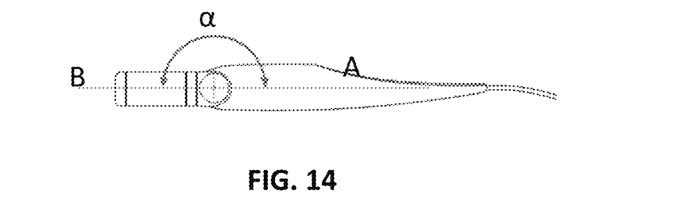

In FIG. 14, the angle α is 180°. In this position, the longitudinal axis A of the detachable tip 11 and the longitudinal axis B of the device 1 are merged.

Figure 15:
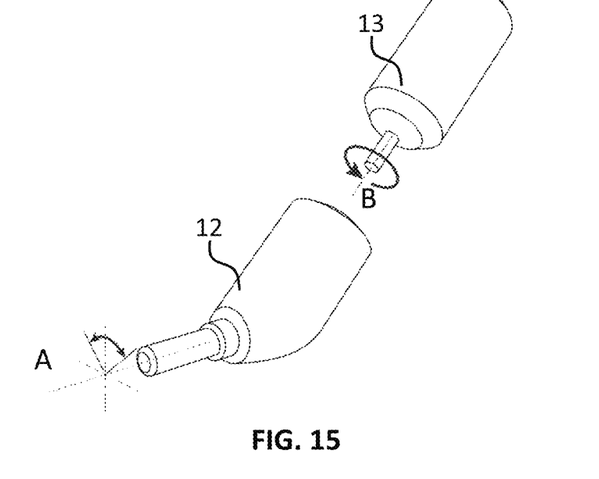
FIG. 15 shows an exploded view of the vibrating means.

FIG. 15 shows the vibrating means in the tip holder. The motor 13 is positioned along the longitudinal axis B of the device 1. The vibrating means drive the tip holder 12 to oscillate according to the rotation frequency of the motor 13.

As the detachable tip 11 is integral with the tip holder 12, the vibration of the tip holder 12 causes the detachable tip 11 to vibrate.

As mentioned above, the device 1 or the base 2 has a vibration control (which corresponds to when the motor 13 is started).

When the device is provided with a switch 14, it can act on the vibrating means (varying the speed of the motor) from 0 rpm to 12,000 rpm. Preferably, two pre-programmed speeds are provided, a first speed of 6,000 rpm and a second speed of 3,000 rpm. The speed of 6,000 rpm corresponds to the microdermabrasion phase and the speed of 3,000 rpm corresponds to the massage phase. The switch also allows the device to be switched off.

When the device does not have a switch 14, the control can be done by the interface 21. The interface 21 has two speeds and/or a speed controller.

In another variant, it is also possible to have all the controls of the interface 21 located on the device 1. Thus, the user can choose whether to use the controls of the interface 21 or of the device.

Figure 16:
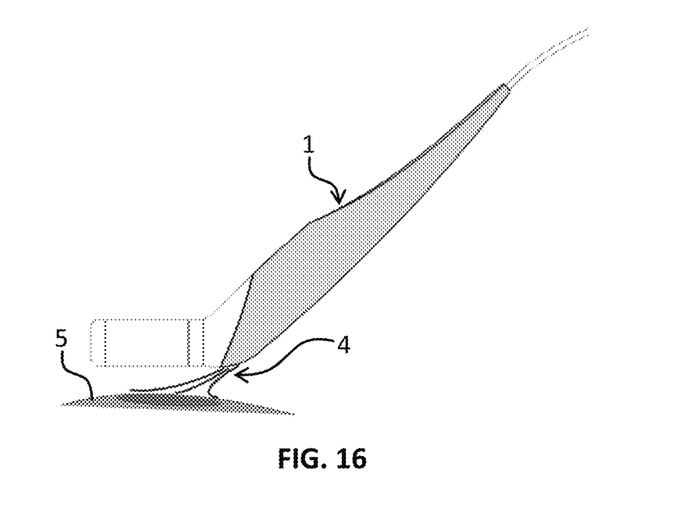
FIG. 16 shows a side view of another example of the device with pulsed air.
Figure 17:
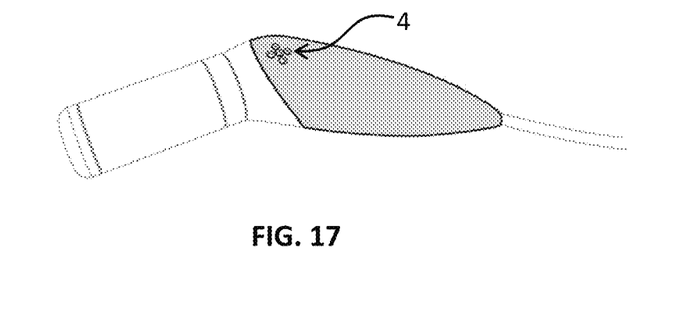
FIG. 17 shows a perspective view of the pulsed air outlet.

FIGS. 16 and 17 show a variant of the device with air pulsed on a treatment area 5. In this manner, the air expulses the dead skin from the treatment area 5 while the device is in operation. FIG. 17 shows the air outlets 4.

It is also possible to have a hermetic device. In this manner, the device can be cleaned with water. Elastic seals are used to create this watertightness and are located on the various elements of the device 1, notably the shell.

Figure 18:
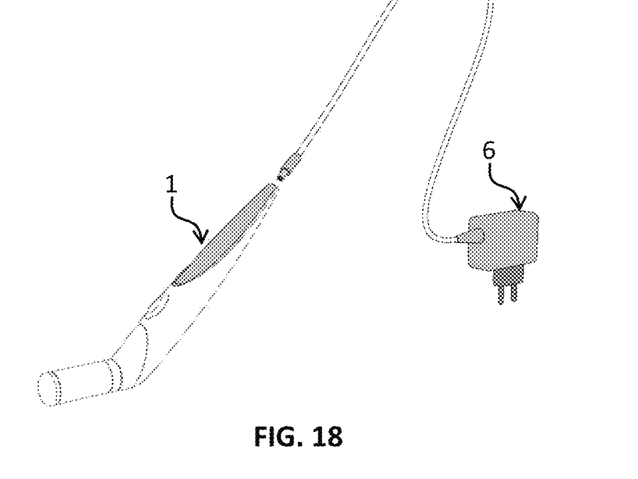
FIG. 18 shows another example of the invention.

FIG. 18 shows another variant of the invention. The device 1, as shown, comprises an internal battery that can be recharged directly by a transformer 6. The connection is made at one end of the device 1 and allows the device 1 to be recharged and/or powered.

Figure 19:
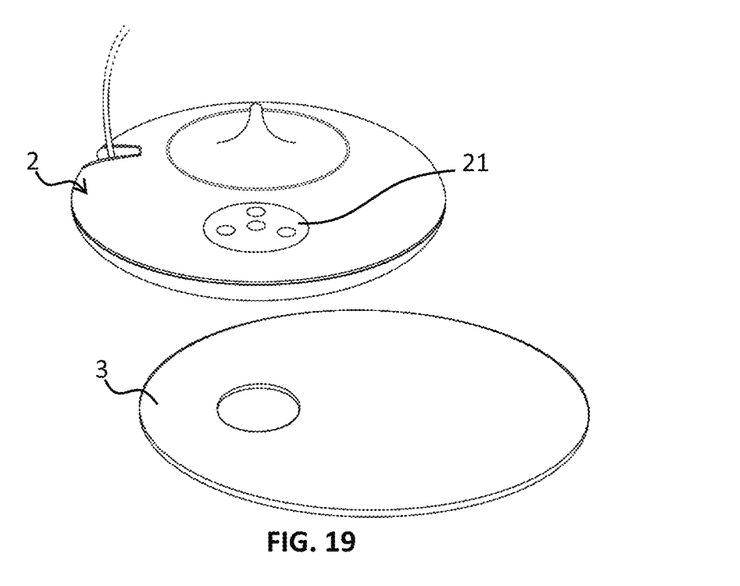
FIG. 19 shows an exploded view of the device according to an example of the invention.

FIG. 19 shows an exploded view of the device 1. The interface 21 and the base 2 are also shown. This figure also shows an accessory tray 3. The accessory tray is secured to the base 2 by two or four screws.

Figure 20:
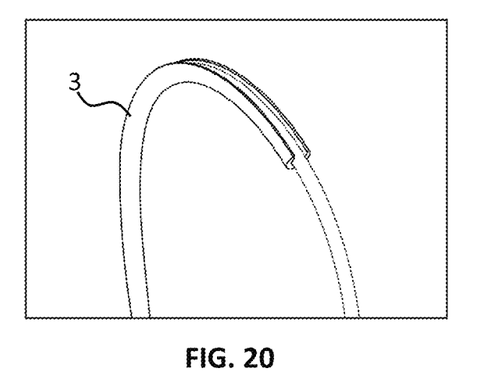
FIG. 20 shows a detailed view of the cable guide of the device according to an example of the invention.

FIG. 20 shows another exemplary embodiment wherein a cable 17 is positioned in a cable guide. The cable guide is cylindrical and comprises a groove in which the cable 17 is positioned.

Figure 21:
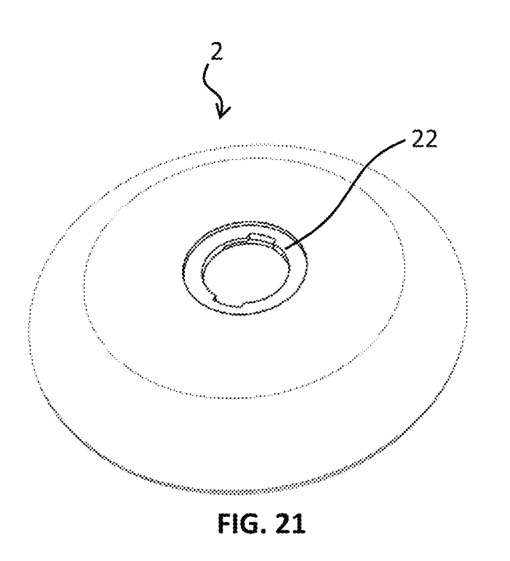
FIG. 21 shows a detailed view of the connecting means of the base.

FIG. 21 shows the connecting means 22. The connecting means 22 is disk shaped and comprises the bayonet to allow it to be locked in position in the base 2. The base 2 shows that the bayonets ensure locking into position. Said position may allow for an electrical connection. To remove the base 2 from its support, it must be rotated a quarter turn in order to remove the bayonets from their housing.

Figure 22:
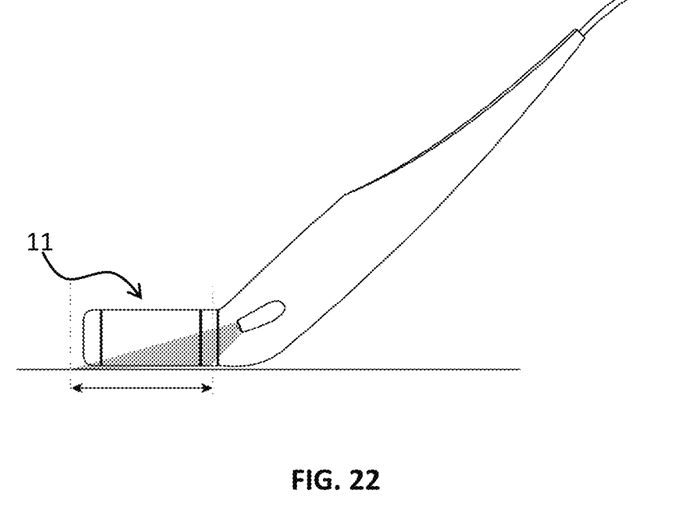
FIGS. 22 and 23 show a side view of an example of the device with two lights.
Figure 23:
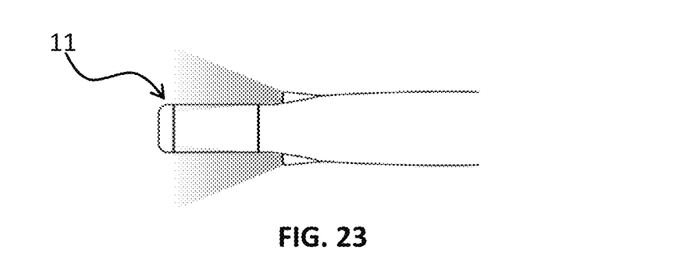

FIGS. 22 and 23 show the location of the LEDs on the side of the device 1. In this manner, the LEDs illuminate at least the entire length of the detachable tip 11 and sides of the detachable tip 11.

The dimensions of the tip may vary depending on the use. For microdermabrasion, the length of the detachable tip 11 may be in the order of 15 to 45 mm, preferably 25 mm for the face and 35 mm for the body. For massage, the length of the detachable tip 11 may be in the order of 15 to 45 mm, preferably 25 mm for the face and 35 mm for the body.

Figure 24:
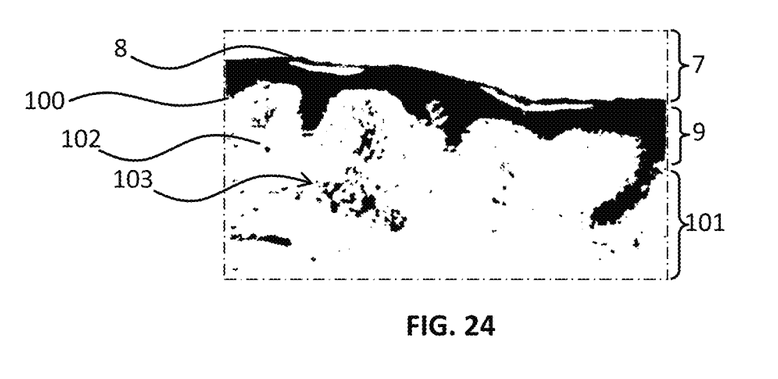
FIG. 24 shows a histological cross section of the skin of a patient prior to application of the device.

FIG. 24 shows a histological cross section of the skin of a patient prior to application of the device 1. The ambient air 7, stratum corneum 8, epithelium 9, basal membrane 100, dermis 101, collagen 102 and microvasculature 103 are shown. The skin is covered with a regular epithelium prior to the first application. The very superficial dermis 101 is somewhat loose. It contains a few vessels and rare mononuclear inflammatory cells.

The skin appears slightly modified after two microdermabrasion sessions. It is somewhat thickened by about 10% with an increase in the number of keratinocytes. In the superficial dermis, a more fibrous appearance is noted at the level of the most superficial collagen. The vessels and the mononuclear inflammatory cells are more numerous.

After four sessions and massage, the epidermis is thickened by about 20% compared to an untreated area. Densification of the superficial dermis is maintained along with neovascularization.

Figure 25:
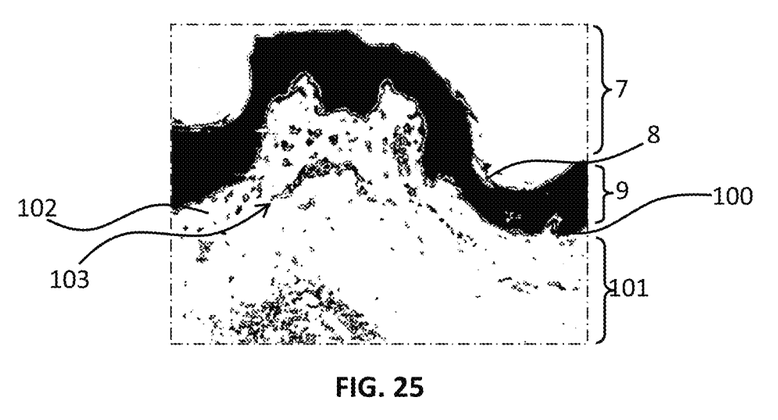
FIG. 25 shows a histological cross section of the skin of a patient after four treatment sessions with the device.

FIG. 25 shows a histological section of the skin of a patient after four microdermabrasion sessions and massage with cream. The ambient air 7, stratum corneum 8, epithelium 9, basal membrane 100, dermis 101, collagen 102 and microvasculature 103 are also shown. The epidermis appears to have increased in thickness. It is assessed at 25%. The superficial collagen also appears denser. Microvasculature persists.

Microdermabrasion causes thickening of the epidermis with inflammatory fibrosis of the superficial dermis. These aspects are increased with the number of sessions.

The application of the cream with the massage amplifies similar effects of the treatment.

It was noted that sensitive skin can be prone to slight dryness in the three days following treatment. The pores are tightened and the skin evened out; these effects last up to three weeks.

The following example relates to the protocol for using the microdermabrasion method.

For the face:

The patient is lying down (or in a slightly raised positioned). The skin of the patient is cleansed which removes all creams. The skin must be as pure as possible in order to get the most benefit from the microdermabrasion phase. The face is then washed (there is no recommended soap, although a non-allergenic, pH-neutral soap is recommended)

and rinsed. The skin must absolutely be no longer wet. Perfectly dry skin ensures optimal efficiency of the microdermabrasion treatment.

A first step of the method is thus a skin preparation, cleaning and drying phase. This may take three to four minutes.

Concerning the microdermabrasion step.

The objective of the microdermabrasion step is to improve skin texture, reduce fine lines, reduce stretch marks, anticipate the effects of ageing on the skin, slow the appearance of imperfections and slow the onset of related irregularities associated with ageing by smoothing the skin.

In an exemplary embodiment, the microdermabrasion step is associated with a light wave (4 seconds for each color, in sequence, yellow-orange-red).

The device is arranged next to the patient. The microdermabrasion step consists in holding the device like a pencil, being careful so as not to obstruct the LEDs with fingers. A detachable tip must first be installed on the device.

The device is then placed in microdermabrasion mode to perform the microdermabrasion treatment. For the face, it is possible to proceed in the following order: 1/right cheek, 2/left cheek, 3/the area in the nasolabial folds (chin, lower lip, upper lip), 4/nose and 5/forehead. One must not pass over the eyes and eyelids or on the red part of the lips.

In another example, the abrasive element 112 has 5 facets. It is the bottom facet which acts when implemented in microdermabrasion mode. Thus, by means of a rotation system it is possible to turn the detachable tip 11 and select another facet of the abrasive treatment element 112: each facet corresponds approximately to a treatment area of 50 to 150 cm$^2$. For the face, each facet will be used for one area: the right cheek is treated, then the tip is turned and a new microdermabrasion facet is used for the left cheek, then the tip is rotated and a new facet is used for the chin/lower white lip and upper lip area (avoiding the red area of the lip), and so forth for the other areas (the face is divided into 5 areas, and each area will be treated by one of the facets of the tip).

To apply the detachable tip on the skin, it is simply placed on the skin resulting in harmless friction (abrasion stops automatically when excessive pressure is applied, due to the flexibility of the skin which begins to vibrate). The gesture may be performed in circles in the clockwise direction; a "disk of three centimeters in diameter" is treated in this manner with twelve passages per disk, rate: one second per turn (one circle per second).

Twelve clockwise circles (disks) are performed on site measuring three centimeters in diameter, at the rate of one circle per second. In other words, each color lasts 4 seconds, thus a color cycle (yellow, orange, red) lasts 12 seconds (and then another yellow, orange, red cycle begins). The user performs approximately 4 circles in the same location for each color, which gives 12 circles for the same disk in 12 seconds. In any case, at the end of a color cycle, the manipulator proceeds to the treatment of the neighboring skin by treating a disk in the adjoining area.

For example, ten to twelve disks are foreseen per cheek, i.e. approximately 120 seconds (2 minutes); for the chin, upper and lower lips=five disks, i.e. approximately one minute; the nose=five disks, i.e. approximately one minute and the forehead=ten to twelve disks, i.e. approximately 120 seconds (2 minutes).

The microdermabrasion treatment step for the face takes approximately eight minutes.

A technical variant (instead of treating in disks) is to perform back and forth movements over a linear area measuring 4 cm in length, with the width of the detachable tip 112, each stroke (back or forth motion) lasting approximately one second, i.e. two round trips per color, i.e. six round trips per color cycle on the same zone, and the zone is changed at the end of the color cycle (giving six round trips, i.e. twelve trips per treated area).

Once the user has finished treating one of the large facial areas (e.g. the right cheek), the user rotates the detachable tip and puts a new facet in position. The user will proceed in the same manner for the left cheek, and for the other areas.

After the microdermabrasion treatment, a cleaning step is performed that removes all impurities and dead skin or imperfections smoothed by the device. Cleaning can be performed using a wipe, which takes approximately one minute.

The massage step, corresponding to the massage phase using the deformable element, improves the quality of the skin in terms of epidermis, vascularization and collagen fiber production. This step enhances the impregnation of the cream on the skin which has been purified, smoothed and stripped bare by the microdermabrasion treatment.

The massage step consists in applying a regenerative, soothing, and astringent cream. This step consists in applying the cream on an area of the face; do not hesitate to add more cream if the gliding sensation is insufficient.

It is necessary to switch to the "massage" mode. The abrasive element must be removed and the deformable element placed on the face in the same sequence as for the microdermabrasion stage.

From a technical standpoint, it is the same as for the microdermabrasion phase except that the duration is longer (e.g. doubled) depending on the type of treatment performed (e.g.: from 8 to 16 minutes depending on the length of treatment for a face). Complete cleaning is then carried out (washing with soap; a neutral, non-allergenic soap is recommended), then rinsing and drying, which can take 3 to 4 minutes.

A variant of the method consists in treating only one area of the face (e.g.: chin, upper and lower lips).

For the rest of the body, the method is the same with the following variables:

a "body" tip with coarser grain is used (180 g/m$^2$) (in comparison with 400 g/m$^2$ for the face);

a greater number of passes, for example, two color cycles, i.e. 24 seconds of treatment per disk, except for the most sensitive areas (hands, inner thighs, around the areolas) where it can stay 12 seconds, i.e. a single color cycle per disk treated;

the surface area treated (entire face=between 200 and 300 cm$^2$)=for the body, using the "body" tip, can be up to 400 cm$^2$, but if the surface area treated is greater, a second tip will be required.

NOMENCLATURE 1 device
11 detachable tip
111 protective element
112 abrasive element
113 deformable element
114 rigid center
12 tip holder
13 motor
14 switch
15 cover
16 shell
17 cable
2 base 21 interface
22 connecting means
3 accessory tray
4 air outlet
5 treatment area
6 transformer
7 ambient air
8 stratum corneum
9 epithelium
100 basal membrane
101 dermis
102 collagen
103 microvascularization
A longitudinal axis of the detachable tip
B longitudinal axis of the device
A angle between the longitudinal axis of the detachable tip and the longitudinal axis of the device

The invention claimed is:

1. A device for microdermabrasion comprising:
    a detachable tip including at least one abrasive element, said abrasive element being provided such as to be applied onto the surface of the skin,
    a body comprising a vibrating means, said vibrating means being capable of making the detachable tip vibrate,
    a tip holder that is securely attached to the body,
    wherein the detachable tip comprises a deformable element positioned between the abrasive element and the tip holder, said detachable tip comprising a protective element positioned at the end of the detachable tip and said protective element being in the shape of a half-sphere or of a flattened half-sphere.

2. The device as claimed in claim 1, wherein the deformable element is made of elastomer with a hardness between 10 and 30, according to the Shore A hardness scale.

3. The device as claimed in claim 1, wherein in a sectional plane to the device containing the longitudinal axis of the body and the longitudinal axis of the tip holder, the longitudinal axis of the tip holder and the longitudinal axis of the body form an angle ($\alpha$) in the order of 90° to 270°.

4. The device as claimed in claim 3, wherein the device comprises a pivot connection between the tip holder and the body of the device, the axis of said pivot connection being contained in a plane orthogonal to the longitudinal axis of the body and passing through a point of intersection of the longitudinal axis of the tip holder with the longitudinal axis of the body.

5. The device as claimed in claim 1, wherein the body of the deformable element is shaped as an oval, a triangle, a square, a polygon of at least five sides or a circle, having a hole in the center into which the tip holder is accommodated.

6. The device as claimed in claim 1, wherein the vibrating means comprises a motor driving in rotation an element equipped with an unbalancing mass.

7. The device as claimed in claim 1, further comprising means for varying the rotation speed of a motor between 0 rpm and 12,000 rpm.

8. The device as claimed in claim 1, further comprising at least lighting means.

9. The device as claimed in claim 1, wherein the deformable element comprises a cavity arranged to receive a volume of a creamy material.

10. The device as claimed in claim 1, further comprising sealing means.

11. The device as claimed in claim 1, wherein the abrasive member is a single use tape arranged to be positioned around the deformable element and a part of said tape is detachable to allow the abrasive element to be removed.

12. The device as claimed in claim 1, wherein the detachable tip is rotatably mobile about the longitudinal axis of the tip holder, and the detachable tip is driven in rotation by a rotating means.

13. A microdermabrasion method for non-therapeutic cosmetic treatments comprising the following steps:
    a) placing a detachable tip on the device as claimed in claim 1,
    b) vibrating the abrasive element on the surface of the skin, for a duration of 1 to 30 minutes over a surface area in the order of 50 to 300 cm$^2$.

14. The method as claimed in claim 13, further comprising a step c), after step b), involving the removal of the abrasive element and the application a soothing cream on the surface of the skin for a period of 2 to 60 minutes.

15. The method as claimed in claim 14, further comprising a step d) prior to step a), involving the removal of the abrasive member from a sealed bag.

16. The device as claimed in claim 3, wherein the angle ($\alpha$) is 135°.

17. The device as claimed in claim 8, wherein the lighting means is a light emitting diode whose wavelength is between 400 and 900 nm and whose fluence is between 3 and 4 J/cm.

* * * * *